United States Patent [19]

Martin

[11] Patent Number: 5,350,358
[45] Date of Patent: Sep. 27, 1994

[54] BENT CO-AXIAL CATHETER

[75] Inventor: Geoffrey S. Martin, Mississauga, Canada

[73] Assignee: Med-Pro Design, Inc., Mississauga, Canada

[21] Appl. No.: 995,213

[22] Filed: Dec. 22, 1992

[51] Int. Cl.$^5$ ............................................. A61M 3/00
[52] U.S. Cl. ...................................... 604/43; 604/280; 604/281
[58] Field of Search ............... 604/43, 175, 29, 280, 604/281, 264, 53, 174, 44, 45, 28, 52, 93, 51, 282, 27, 39, 158, 283, 284, 96, 194; 606/191, 192, 194

[56] References Cited

U.S. PATENT DOCUMENTS

| | | |
|---|---|---|
| 4,411,055 | 10/1983 | Simpson et al. |
| 4,687,471 | 8/1987 | Twardowski et al. ............ 604/175 |
| 4,895,561 | 1/1990 | Mahurkar ............... 604/43 |
| 5,057,075 | 10/1991 | Moncrief et al. ............ 604/49 |
| 5,156,592 | 10/1992 | Martin et al. ............ 604/43 |
| 5,167,623 | 12/1992 | Cianci et al. ............ 604/43 |
| 5,250,041 | 10/1993 | Folden et al. ............ 604/284 |
| 5,254,107 | 10/1993 | Soltesz ............... 604/282 |

FOREIGN PATENT DOCUMENTS

| | | | |
|---|---|---|---|
| 146777 | 6/1984 | Denmark ............... B65B 55/08 |
| 0081724 | 6/1983 | European Pat. Off. ..... A61M 25/00 |
| 0087402 | 8/1983 | European Pat. Off. ..... A61B 10/00 |
| 0098688 | 1/1984 | European Pat. Off. ..... A61M 25/00 |
| 0129634 | 1/1985 | European Pat. Off. ..... A61M 25/00 |
| 0168136 | 1/1986 | European Pat. Off. ..... A61M 1/30 |
| 0101890 | 9/1986 | European Pat. Off. ..... A61M 1/34 |
| 0306010 | 3/1989 | European Pat. Off. ..... A61M 25/00 |

*Primary Examiner*—C. Fred Rosenbaum
*Assistant Examiner*—Vanitha Alexander
*Attorney, Agent, or Firm*—Rogers & Scott

[57] ABSTRACT

The invention provides a co-axial dual lumen catheter having a main section, a tip section, and a U-shaped proximal portion extending from the main section, and ending at a junction where intake and outlet tubes are connected to the proximal portion. An inner tube extends from the junction to the tip of the catheter to define a return lumen, and combines with outer tubes in the main section and the proximal portion to define an intake lumen. The inner tube is thin walled relative to the wall thickness of a first outer tube used in the main section, and a second outer tube used in the proximal portion has a greater cross-sectional area than the first outer tube. A proximal end structure is also described in which the intake and outlet tubes extend generally parallel with the main body and to one side of the main body.

20 Claims, 4 Drawing Sheets

BENT CO-AXIAL CATHETER

This invention relates to co-axial dual lumen catheters for use in haemodialysis treatments and more particularly to such a catheter for placement in a jugular vein.

Haemodialysis treatments have been developed since the early 1960s using a variety of combinations and arrangements of catheters. The earliest treatments were conducted using two needles in the same vein and this subsequently led to pioneer work done by Dr. Shaldon in England who used two flexible catheters which could be left in place for limited periods. It was recognized by some practioners that it would be preferable to use a single incision rather than to use two and this led to the development of techniques involving dual flow catheters. There are two basic types. The first to be attempted was a co-axial catheter with the intake lumen surrounding the return lumen. While this had advantages, there were some difficulties of manufacture. The other approach is to use side-by-side lumens either in individual tubes connected to one another or in a single tube divided by an interior septum so that the lumens are D-shaped. Although such structures have become popular with many surgeons, they also had disadvantages. The most notable disadvantage is that because the lumens are side-by-side, the intake openings must be in one side of the catheter. As a consequence of this, there is a tendency for the suction at the opening to draw the catheter towards the wall of a blood vessel with the result that the flow could stop. Medical staff then have to move the catheter by rotating it until blood again flows.

The side-by, side structures have advantages in manufacture due to the fact that the two lumens can be created simultaneously in an extrusion. This has led to great activity in developing devices having side-by-side D-shaped lumens at the expense of co-axial structures. Nevertheless, due to the inherent disadvantages of the side-by-side structures, there has been renewed interest in developing suitable co-axial devices. This is primarily because the intake lumen can have openings in any part of the wall of the catheter.

Dialysis catheters are commonly inserted in either the subclavian or jugular veins. It has been found that the subclavian vein is more desirable from the standpoint of patient acceptance due primarily to the fact that the proximal (i.e. external) portions of the catheter can be readily taped to the patient without interfering significantly with the patient's movements. However, it has been found that jugular placement has resulted in less vein stenosis, and consequently jugular placement is finding more favour among surgeons although the proximal portions of the catheter can be an irritant for the patient because the portions tend to project upwardly near the ear of the patient.

It is therefore an object of the present invention to provide a co-axial catheter particularly for placement in a jugular vein and which has a minimal upwardly projecting proximal portion.

It is also an object of the invention to provide such a catheter which will also permit periodic rotation of the catheter in place to ensure continued patency.

Accordingly, in one of its aspects, the invention provides a dual lumen catheter having a main body, a tip section at a distal end of the main body, an attachment positioned on the main body for fixing the catheter relative to the patient, a proximal U-shaped portion extending from the attachment, a junction at a proximal end of the U-shaped portion, and a pair of tubes attached to the junction and forming continuations of the respective lumens for coupling the catheter to dialysis equipment.

This and other aspects of the invention will be better understood with reference to the drawings and the following description, in which.

Figures 1, 2:
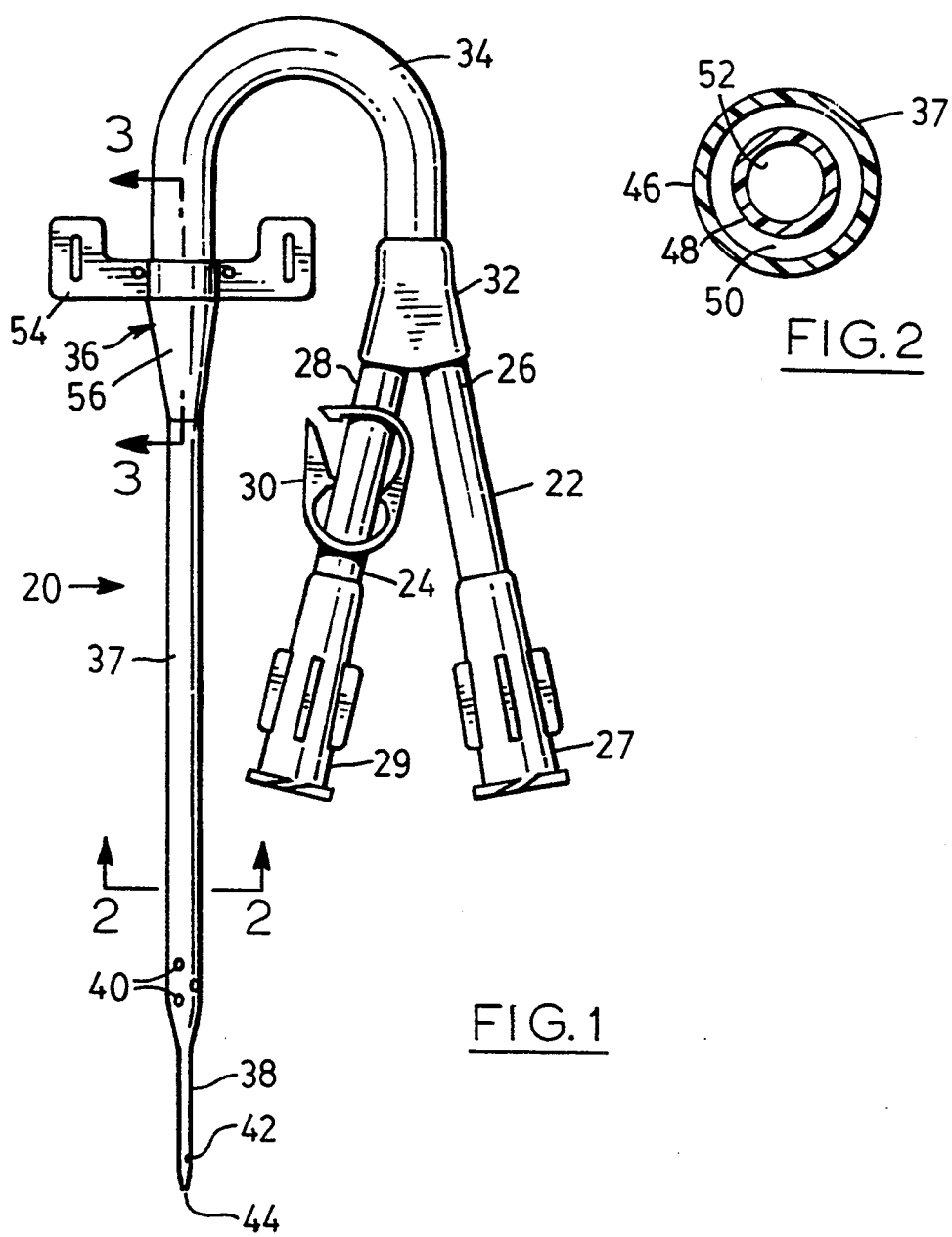
FIG. 1 is a side view of a catheter a according to a preferred embodiment of the invention.
FIG. 2 is a sectional view on line 2—2 of FIG. 1 and drawn to a larger scale.

Reference is made firstly to FIG. 1 which illustrates a co-axial catheter designated generally by the numeral 20 and useful for withdrawing blood through an intake 22 and returning treated blood through an outlet 24. The intake and outlet include prospective flexible tubes 26, 28 which can be clamped using conventional devices such as device 30 shown on tube 28 and which terminate at respective luer connectors 27, 29. The tubes meet at a junction 32 at the proximal end of a U-shaped proximal portion 34 which terminates at its distal end in a proximal transition portion 36 leading to a main section 37 and hence to a tip section 38 which meets the main body at a distal transition portion 39. Blood is withdrawn through side openings 40 and returns through further side openings 42 and end opening 44. As a result of this arrangement the tubes 26, 28 extend generally in parallel with the main section 37 and lie to one side of the section 37.

As seen in FIG. 2, the main section 37 includes an outer tube 46 containing an inner tube 48 which also extends through an outer tube 60 in the proximal portion 34 as will be explained. The inner tube 48 is therefore continuous having a first part inside outer tube 46 in the main section 37 and the second part inside the outer tube 60 forming part of the proximal portion 34. The inner tube 48 is free but for attachments at its ends as will be explained. The openings 40, shown in FIG. 1, supply blood to an intake lumen 50 formed between the tubes 46, 48 and, in the proximal portion, between tubes 60 and 48. Blood returns by a return lumen 52 defined by the inner tube 48. The junction 32 at the proximal end of the U-shaped proximal portion 34 connects tubes 48, 60 to the tubes 26, 28 (as will be explained) and the catheter is completed by provision of an attachment in the form of a wing structure 54 used to hold the catheter in place in a patient in conventional fashion. It is preferable that the wing structure be rotatable on the catheter and provision is made for this with longitudinal location provided by a tapered sleeve 56 and a distal end of the portion 34. These parts are elements of the transition portion 36 as will be explained with reference to FIG. 3.

The side openings 40 and 42 are typical of openings that can be provided around the periphery of the catheter to ensure flow into and out of the catheter from anywhere about the catheter. Consequently, if the catheter should be positioned so that some of the openings are occluded by engagement with the wall of a vein, other openings will provide the essential flow.

Figure 3:
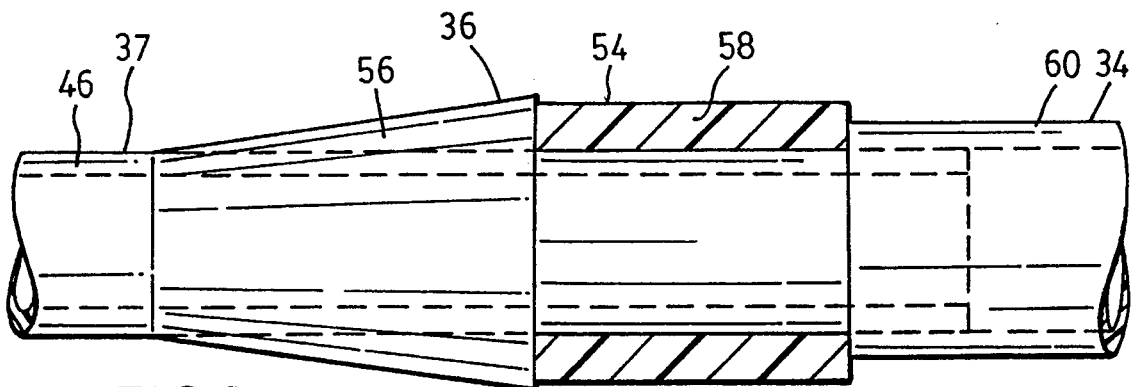
FIG. 3 is a sectional view on line 3—3 of FIG. 1 and drawn to the same scale as FIG. 2.

Reference is next made to FIG. 3 to describe a preliminary step in the manufacture of the catheter. As seen in FIG. 3, outer tube 46 extends through the tapered sleeve 56, then through a tubular central part 58 of the wing structure 54, and ends inside a distal end of the outer tube 60 of the proximal portion 34. Details of this arrangement will become evident as the method of assembly is described.

As a preliminary, the outer tube 46 is placed in a suitable conventional injection moulding machine and positioned suitably to mold the sleeve 56 about the tube. The materials are compatible thermoplastics so that the sleeve becomes an integral part of the tube 46. Next, the outer tube is used in an assembly shown in FIG. 4. In this step the inner tube 48 has a leading part indicated by numeral 68 within a corresponding part 70 of the tip section 38. These parts can of course be deformed to fit together in this way, but as shown, round tubing is selected for these parts so that they fit within one another quite readily but at the same time quite closely. If preferred, the parts can be attached to one another using a suitable adhesive. Typically the inner tube is #6 French and the tip section #8 French. After this step has been completed, the outer tube 46 is placed about the inner tube 48 and a leading part 72 of the outer tube overlaps part 70 of the tip section. Consequently the parts 68, 70 and 72 are located about one another. Again an adhesive can be used to fix the assembly.

A tubular cylindrical mandrel 74 is proportioned to fit inside the outer tube 46 and about the inner tube 48. Typically the outer tube is #12 French and the materials of all of the inner and outer tubes and the tip section are polyurethane with the selection of the materials being chosen to give the physical characteristics desired. For instance if a soft tip is required, then a material of a suitable Durometer is provided for the tip section 38 and of course sufficient rigidity must be provided in the outer tube 48 to ensure that the catheter is stable during insertion and when in place. It should be noted that the inner tube is protected to some extent against collapse by the outer tube so that the inner tube can be of a relatively soft thin walled polyurethane. As will be described, this assists in forming the U-shaped proximal portion 34 as well as maximizing the space available for flow in the catheter.

A solid second mandrel 76 is provided to support the inner tube so that this tube extends between the mandrels 74 and 76. Mandrel 74 has a rounded end and stops against the part 70 of the tip section 38 whereas the inner mandrel 66 projects into the tip section 38. This provides support along the space occupied by two halves of a mold 78 which are operable to move into contact with the assembly.

Figure 4:
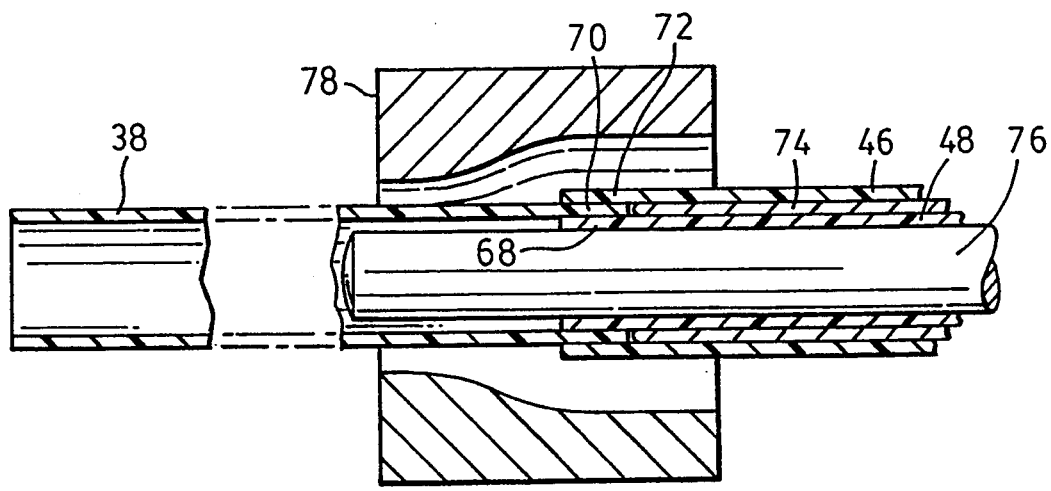
FIGS. 4 and 5 are diagrammatic views illustrating steps in the procedure of manufacturing the distal end (tip end) of the catheter.

The mold 78 is used to form the transition portion 39 by moving the mold halves into contact with the assembly shown in FIG. 4 under the influence of heat and pressure sufficient to cause the material of the parts 68, 70 and 72 to flow. Once this is completed the structure is allowed to cool and the mandrels removed. The result is shown in FIG. 5.

Figure 5:
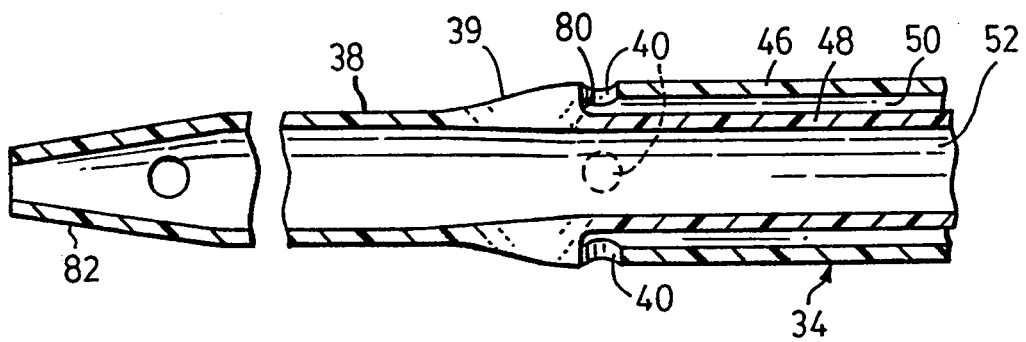

As seen in FIG. 5, the intake lumen 50 terminates at a blind annular end wall 80 at the transition portion 39. The intake lumen 50 is contained between outer tube 46 and inner tube 48 and the openings 40 are provided immediately adjacent the transition portion 39 to allow blood flow into the lumen 50. More openings can of course be provided further away from the transition portion (as seen in FIG. 1) if required.

The return lumen 52 formerly described with reference to the inner tube 48, now continues through the transition portion, 39 and through the tip section 38. The transition portion ends the intake lumen 50 and blends smoothly from the outer surface of the tip section to the outer surface of the main section, and in particular to the outer surface of the outer tube 46.

It should be noted in FIG. 5 that the three parts, namely the outer and inner tubes 46, 48 and the tip section 38, are shown as three individual parts by the shading. Where they meet at the transition portion 39, the shading has been omitted because this is a portion where the materials flow into one another and it is indefinite where the parts begin and end after molding. However by comparison between FIGS. 4 and 5 it is evident that the parts 68, 70 blend into one as do the parts 70 and 72 resulting in the transition portion 36. Preferably, the parts are all polyurethane with the grades and sizes being chosen to provide the desired physical characteristics such as a soft pliable tip section and a stiffer outer tube with a thin walled inner tube.

After the assembly has been molded as demonstrated in FIGS. 4 and 5, the tip section 38 is deformed in a conventional manner to create a tapered tip 82 about the end opening 44.

Next the proximal transition portion 36 is completed. Referring to FIG. 3, the standard wing structure 54 is slipped over the outer tube 46 into engagement with the tapered sleeve 56. Next the proximal outer tube 60 of the U-shaped proximal portion 34 is slipped over the inner tube 48 (not shown in FIG. 3) and engaged on the tube 46. The tube 60 is held in place by chemical bonding or heat sealing in a position which permits the wing structure to rotate. This assembly takes place before the tube 60 is bent. It should be noted that the numeral 54 could also indicate a conventional cuff which would be located in the same way as the wing structure.

Figure 6:
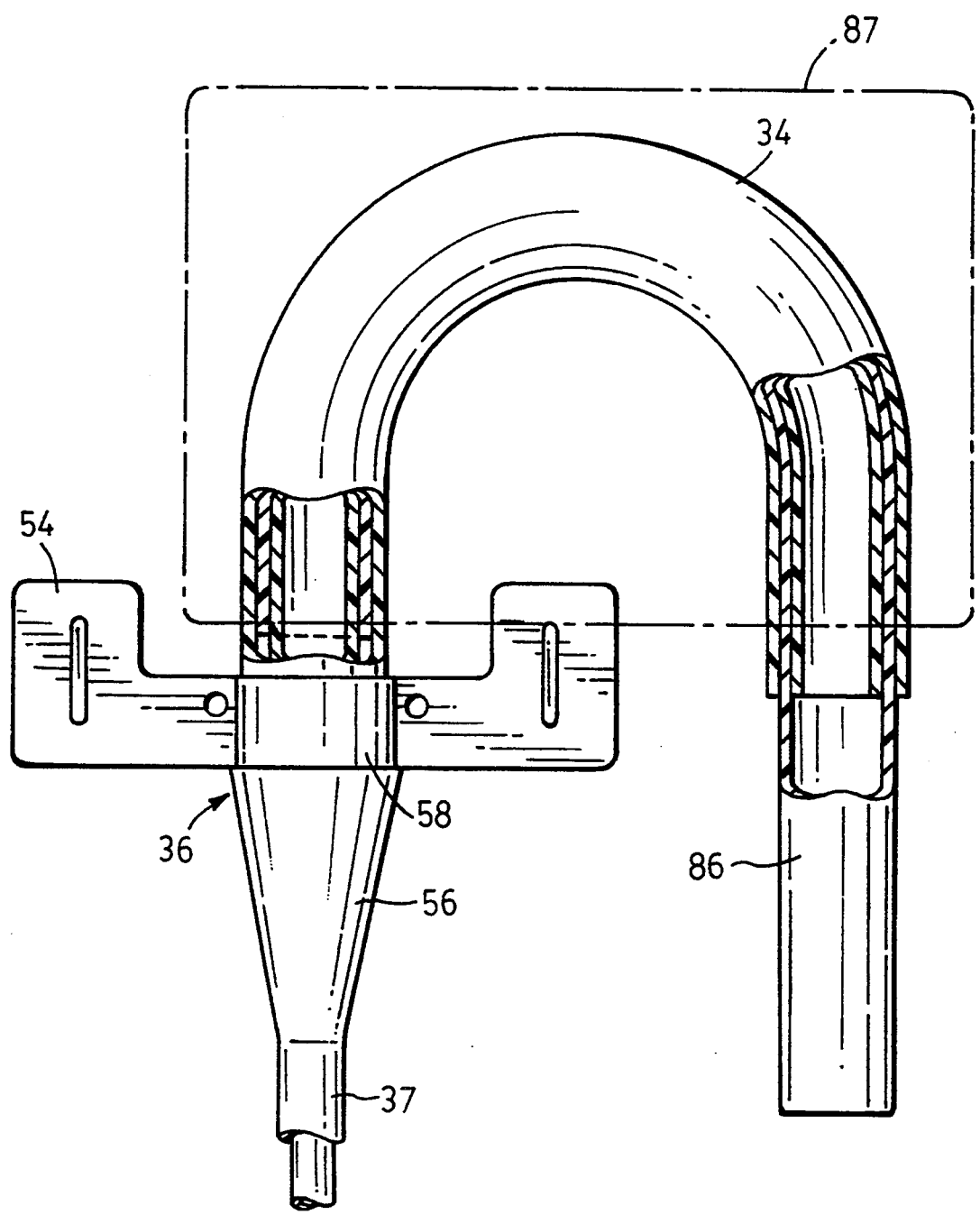
FIG. 6 is a sectional view to a larger scale than that used for FIG. 1 and illustrating a step in the manufacture of a U-shaped proximal portion of the catheter.

The assembly is now complete from the proximal transition portion 36 to the distal end of the catheter. The outer tube 60 of the portion 34 contains part of the inner tube 48 which, as was described, ends at and is anchored in, the distal transition portion 39. The next step is to give the proximal portion 34 its U-shape. To do this, a flexible tubular mandrel indicated as 86 in FIG. 6 is engaged over the inner tube 48 and inside the outer tube 60. The mandrel is of a synthetic elastomeric material, preferably that sold under the trademark TEFLON.

As seen in FIG. 6, the mandrel 86 is pushed until it reaches the proximal transition portion 36 and then the portion 34 is curved manually to fit into a die indicated diagrammatically by numeral 87. This die has a channel to receive the portion 34 and a similar second part of the die closes over the first part to trap the portion 34 in the desired U-shaped configuration. The die and catheter are then subjected to heating to about 120 degrees C. (250 degrees F.) to cause the inner and outer tubes to take a new set. The mandrel resists this temperature.

After cooling in the die, the proximal portion 34 has a U-shaped configuration as seen in FIGS. 1 and 6.

Figure 7:
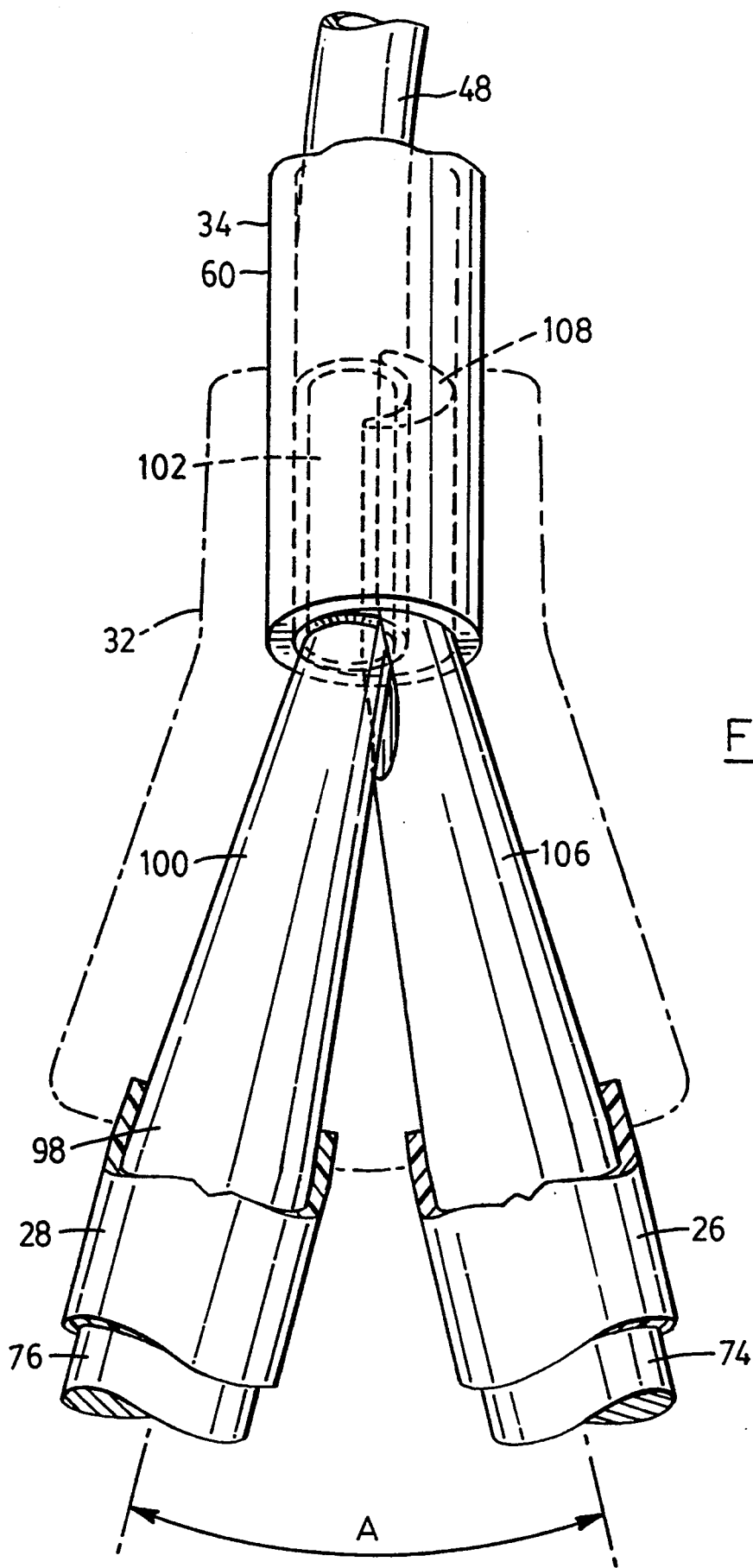
FIG. 7 is a partially sectioned view to a scale larger than that used for FIG. 1 and showing a junction at the proximal end of the catheter and demonstrating both the structure and the method of making the junction.

The last step is to form the proximal end structure or junction 32 reference is now made of FIG. 7. After trimming the inner and outer tubes 48, 60 as required, the assembly is prepared by first positioning a proximal end of the proximal portion 34 in a mold (not shown) which is to create the junction 32 by injection molding using conventional techniques. The portion 34 is positioned using first and second mandrels 94, 96. The mandrel 96 has a cylindrical portion 98 blending into a converging generally conical portion 100, which in turn blends into a cylindrical end part 102 angled with respect to the portion 100. The part 102 fits closely inside a proximal end of the inner tube 48 and this tube is maintained in a position in engagement with the outer tube 60 by the mandrels 94, 96.

The mandrel 94 has an outer cylindrical portion 104 which blends into a converging and generally conical portion 106 ending at a projection 108. This projection has a generally U-shaped cross-section (as will be explained) and is angled with respect to the conical portion 106.

The projection 108 on the end of the mandrel 94 is shaped to fit the space provided when the inner tube 48 is held against the inner surface of the outer tube 60. As a result it has a generally U-shaped configuration. The angular offsets of the projection 108 and the end part 102 of lumen 96 result in the projection and end part 102 extending in parallel axially with respect to the proximal portion 34. The cylindrical portions 98 and 104 diverge sufficiently with respect to the axial main section that the ends of the respective intake and outlet tubes 26, 28 can be accommodated on the mandrels with the ends positioned in the mold to become entrapped in the junction 32.

Once the assembly shown in FIG. 7 has been completed, the mold is closed and injection takes place to form the junction 32. The material is preferably polyurethane although other materials can be used provided that the usual requirements of compatibility etc. are met.

The mandrels are removed, and because there is some flexibility in the material, the mandrels can be pulled out without causing any damage.

The structure shown in FIG. 7 has particular significance in the resulting flow through the catheter. Unlike previous co-axial catheters, the flow tends to remain linear due to the fact that the intake and return tubes 26, 28 are generally in line with the portion 34. Previously, one of these tubes was in line and the other was connected through the side of the junction so that the flow must pass through a significant angle which in some instances approached 90 degrees. This is most undesirable because any changes in direction of this kind will result in turbulence in the blood flow with potential for damage to the blood. It is well established that pressure fluctuations in blood flow paths should be minimized, and this structure tends to limit such variations.

The angle shown as "A" in FIG. 7 indicates the divergence between the tubes 26, 28 as they meet the junction 32. Because of the construction it is possible to maintain this angle in the order of 15 to 20 degrees and is readily maintained below 30 degrees. As a result, the flow into and out of the catheter is essentially axial with reference to the portion 34 at all times. This is because the angle of each of the tubes 26, 28 with reference to the axis of the portion 34 where it meets the junction 32 is half of the range up to 30 degrees.

The catheter is now complete but for the final shaping of the proximal portion 34. Up to this point this portion has remained straight and consists of the outer tube 60 and part of the inner tube 48 which starts at the junction 32 (FIG. 1) and ends at the distal transition portion 39.

Reference is now made to FIG. 7 to describe forming the proximal portions 34.

The catheter shown as a preferred embodiment is typical of catheters that could be made in accordance with the invention. As mentioned earlier it is possible to proportion the tip and/or provide soft material for the tip to ensure that after insertion the tip will flex and will not damage veins. At the same time, there is sufficient rigidity in the transition portion to maintain the relationship between the tip and the inner and outer tubes so that the intake lumen 50 remains patent while the insertion takes place and during use.

It will be apparent that the structure can be varied within the scope of the invention. In particular, the tip section need not be tapered and in some cases (depending upon requirements) the distal end of the catheter could be closed. Also, the proximal transition portion could be arranged with a cuff instead of the wing structure 20. Either of these attachments can be used advantageously.

The proportions of the parts can be varied and it would be possible to do some preforming before assembly.

In a typical embodiment the various tubes used in the structure are polyurethane. The outer tube 46 is a firm polyurethane having a 65D Durometer. It is 3.175 mm inside diameter and 3.734 mm outside diameter. The tip section is also 65D with an inside diameter of 1.727 mm and an outside diameter of 2.667 mm. The inner tube is of a soft thin walled polyurethane dimensioned to fit into the assembly shown in FIG. 3, and the tube 60 is proportioned to fit over the outer tube 46. The tube 60 has a wall thickness of about 1.31 mm and a hardness of 85A to minimize the risks of kinking and to protect the inner tube.

It is important to note that this catheter overcomes disadvantages in the art. Firstly, the structure is such that the inner tube can be thin walled because it is protected by the stiffer outer tube 46 in the main section 37 and by the outer tube 60 in the curved proximal portion 34. The thin-walled soft inner tube takes up minimal cross-sectional space thereby permitting the portion of the co-axial catheter which is to be inserted to have a smaller cross-section. Another feature is the fact that there is a minimum of upwardly extending structure beyond the attachment 36 when the catheter is placed in a jugular vein. This is very important to the comfort of the patient. Also, because attachment takes place where the catheter exits the incision, manipulation of the tubes to make connections etc. will have less likelihood of dislodging or moving the catheter.

The invention incorporates all variations within the scope of the claims and is not restricted to the embodiments disclosed.

I claim:

1. A co-axial dual lumen catheter comprising:
   a main section having proximal and distal ends and including a first outer tube;
   a tip section at said distal end;
   an attachment at said proximal end for anchoring the catheter to a patient immediately adjacent an incision where the catheter entry is effected;
   a U-shaped proximal portion having a distal end attached to the main section at said proximal end of the main section and having a proximal end, the proximal portion including a second outer tube;

a junction attached to the proximal end of the proximal portion;

an inner tube extending loosely inside the first and second outer tubes and anchored at the tip and the junction to define a return lumen and combining with the first and second outer tubes to define an annular intake lumen;

intake and outlet tubes attached to the junction, the tubes extending generally in parallel with the main section and to one side of the main section and being coupled to the respective intake and return lumens; and the inner tube being thin walled relative to the wall thickness of the first outer tube, and the second outer tube having a greater cross-sectional area than the first outer tube.

2. A catheter as claimed in claim 1 in which the attachment is a wing structure.

3. A catheter as claimed in claim 1 in which the attachment is a cuff.

4. A catheter as claimed in claim 1 in which the first outer tube defines intake openings providing access into the intake lumen, and the tip section is of smaller cross-section than the main section, the tip section having at least one return opening.

5. A catheter as claimed in claim 4 and further comprising a transition portion at the distal end of the main section, the transition portion being formed of material provided in overlapping parts of the inner tube the tip section and the first outer tube, the inner tube being inside the tip section which is inside the first outer tube, the inner tube blending smoothly internally into the tip section at the transition portion and the outer tube blending smoothly externally into the tip section with the intake lumen ending at the transition portion, the tip section forming a continuation of the return lumen and the return lumen ending at said return opening.

6. A catheter as claimed in claim 5 in which the inner tube and the first outer tube are spaced from one another radially where the intake lumen terminates.

7. A catheter as claimed in claim 5 in which the transition portion is tapered smoothly to converge from the first outer tube to the tip section.

8. A catheter as claimed in claim 4 in which the inner tube, first and second outer tubes and tip section are round in cross-section.

9. A catheter as claimed in claim 8 in which the diameter of the tip section is greater than that of the inner tube and less than that of the first outer tube.

10. A co-axial dual lumen catheter comprising:
a main section having proximal and distal ends and including a first outer tube, the first outer tube extending along a longitudinal axis and defining intake openings;

a U-shaped proximal section attached to the proximal end of the main section, the proximal section including a second outer tubes;

an inner tube extending through the first and second outer tubes; the inner tube defining a return lumen and combining with the first and second outer tubes to define an annular intake lumen;

intake and outlet tubes;

a junction coupling the intake and outlet tubes to the proximal section with the intake tube coupled for receiving blood from the intake lumen and the outlet tube coupled for delivering treated blood to the return lumen; and the intake and outlet tubes leaving the junction generally parallel with the main section and to one side of the main section and with an angle of divergence between the intake and the outlet tubes of less than about 30 degrees and spaced substantially equally to either side of an extension of said axis.

11. A catheter as claimed in claim 10 in which the angle of divergence is about 15 to 20 degrees.

12. A catheter as claimed in claim 10 in which the inner tube is located against the second outer tube inside the junction.

13. A co-axial dual lumen catheter for use in dialysis, the catheter comprising:
a main section for insertion and having a selected cross-section;

a tip section of smaller cross-section than the selected cross-section and attached to a distal end of the main section;

a U-shaped proximal section extending from a proximal end of the main section and having a cross-section greater than said selected cross-section;

the main section having a first outer tube of a selected wall thickness and having said selected cross-section and the proximal section having a second outer tube having a wall thickness greater than said selected wall thickness;

an inner tube extending from the tip section through the first and second outer tubes and having a wall thickness less than said selected wall thickness whereby an intake lumen is defined in the space between the inner tube and the first and second outer tubes, and a return lumen is defined by the inner tube and the tip section; and a junction coupled to the inner tube and the second outer tube to facilitate connecting the catheter to dialysis equipment.

14. A catheter as claimed in claim 13 and further comprising a distal portion where the inner tube, tip section, and first outer tube of the main section meet, the transition portion presenting a smooth tapered outer surface to facilitate insertion.

15. A co-axial catheter as claimed in claim 13 in which said junction includes intake and outlet tubes, the tubes being connected respectively to the intake and return lumens and lying generally parallel to the main section and to one side of the main section.

16. A catheter as claimed in claim 13 in which the inner tube, first outer tube and tip section are round in cross-section.

17. A catheter as claimed in claim 13 in which the tip section includes an opening at the distal end of the catheter.

18. A catheter as claimed in claim 13 in which the inner tube and the first outer tube are spaced from one another concentrically where the intake lumen terminates.

19. A catheter as claimed in claim 18 in which an end part of the inner tube is engaged inside a part of the tip section which in turn is engaged inside a part of the first outer tube to form a transition portion, and in which the transition portion is tapered smoothly to converge from the first outer tube to the tip section.

20. A dual lumen catheter as claimed in claim 19 in which the tip section is more flexible than the main section.

* * * * *